US00PP34621P2

(12) United States Plant Patent
Stoppel

(10) Patent No.: US PP34,621 P2
(45) Date of Patent: Oct. 4, 2022

(54) SWEET CHERRY TREE NAMED 'PRIM 22'

(50) Latin Name: ***Prunus avium* (L.) L.**
Varietal Denomination: Prim 22

(71) Applicant: Cerasina GmbH, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 17/803,074

(22) Filed: Feb. 2, 2022

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./180, 181, 182
See application file for complete search history.

*Primary Examiner* — Susan McCormick Ewoldt
(74) *Attorney, Agent, or Firm* — Myers Bigel, P.A.

(57) ABSTRACT

'Prim 22' is a new and distinct variety of sweet cherry tree which is characterized by producing large size dark red fruits having an angular to oblate shape. The fruits of 'Prim 22' ripen early. They are medium firm with medium acid having a pleasant cherry flavor and strong stem attachment. 'Prim 22' fruits have medium shelf-life.

4 Drawing Sheets

Latin name of the genus and species: The Latin name of the novel plant variety disclosed herein is *Prunus avium* (L.) L.

Variety denomination: The inventive variety of the *Prunus avium* (L.) L. disclosed herein has been given the varietal denomination 'Prim 22'.

BACKGROUND OF THE INVENTION

The present invention relates to a new and distinct variety of sweet cherry tree which is characterized by producing large size dark red fruits having an angular to oblate shape. 'Prim 22' fruits ripen early, are medium firm with medium acid and have a pleasant cherry flavor and a strong stem attachment. 'Prim 22' fruits have medium shelf-life. The taste and brix of the fruits are significantly better when the tree is grown in warm location.

The new and distinct cherry variety described and claimed herein was developed in 2007 in Baden-Wuerttemberg, Germany and originated from open pollinated seeds of fruits of the female parent 'Tieton' (U.S. Plant Pat. No. 8,051, also known as 'PC 7144-7'). The male parent is unknown. The present variety of sweet cherry plant was selected as a single plant and was first asexually propagated in February 2008 by grafting on 'Gisela 5' rootstock (U.S. Plant Pat. No. 9,622) in Kressbronn, Baden-Wuerttemberg, Germany.

'Prim 22' is believed to be most similar to the cherry variety 'Prim 25' (U.S. Plant Pat. No. 33,719). 'Prim 22' is distinguished from 'Prim 25' (U.S. Plant Pat. No. 33,719) at least in tree habit, ripening time and fruit shape. Both varieties have a shiny dark red fruit color and a high fruit firmness. 'Prim 22' differs from 'Prim 25' in having a weaker tree growth and having branches that are more likely to droop. The ripening time for 'Prim 22' is about 3 days earlier than that for 'Prim 25'.

When compared to its female parent, 'Teiton', 'Prim 22' exhibits a fruit ripening time that is about 7 days earlier than 'Tieton'. In addition, 'Prim 22' has a different fruit shape and tree habit than 'Tieton'. Specifically, the fruits of 'Tieton' are broadly cordate, in comparison to 'Prim 22', which has angular to oblate fruits, and Tieton's growth habit is vigorous and spreading while Prim 22 growth habit is drooping and weak. 'Prim 22' has a dark red fruit color and firmness that is very similar to 'Tieton'.

Asexual reproduction of this new variety by grafting and budding onto rootstock shows that the foregoing and all other characteristics and distinctions described herein remain true to type and are established and transmitted through successive propagations. All asexual reproduction was carried out in Kressbronn, Baden-Wuerttemberg, Germany. 'Prim 22' has not been evaluated under all possible environmental conditions. The phenotype may vary with variations in environment without a change in the genotype of the plant.

SUMMARY OF THE INVENTION

The new sweet cherry variety, 'Prim 22,' is characterized by producing large angular to oblate shaped fruits having a dark red color. The fruits of 'Prim 22' ripen in medium early time, about 3 days after 'Burlat' (unpatented). The fruits of 'Prim 22' are firm with a good cherry flavor. 'Prim 22' produces a good yield of high-quality fruits. The taste and appearance of the fruits of 'Prim 22' are best when grown in a hot dry climate.

BRIEF DESCRIPTION OF THE PHOTOGRAPHS

This new cherry tree is illustrated by the accompanying photographs which show the plant's foliage and inflorescences. The colors shown are as true as can be reasonably obtained by conventional photographic procedures. Colors in the photographs may differ slightly from the color values cited in the detailed botanical description, which accurately describe the colors of the new cherry tree. The accompanying photographic drawings illustrate the new variety at approximately 7 years of age.

DETAILED BOTANICAL DESCRIPTION

Figure 1:
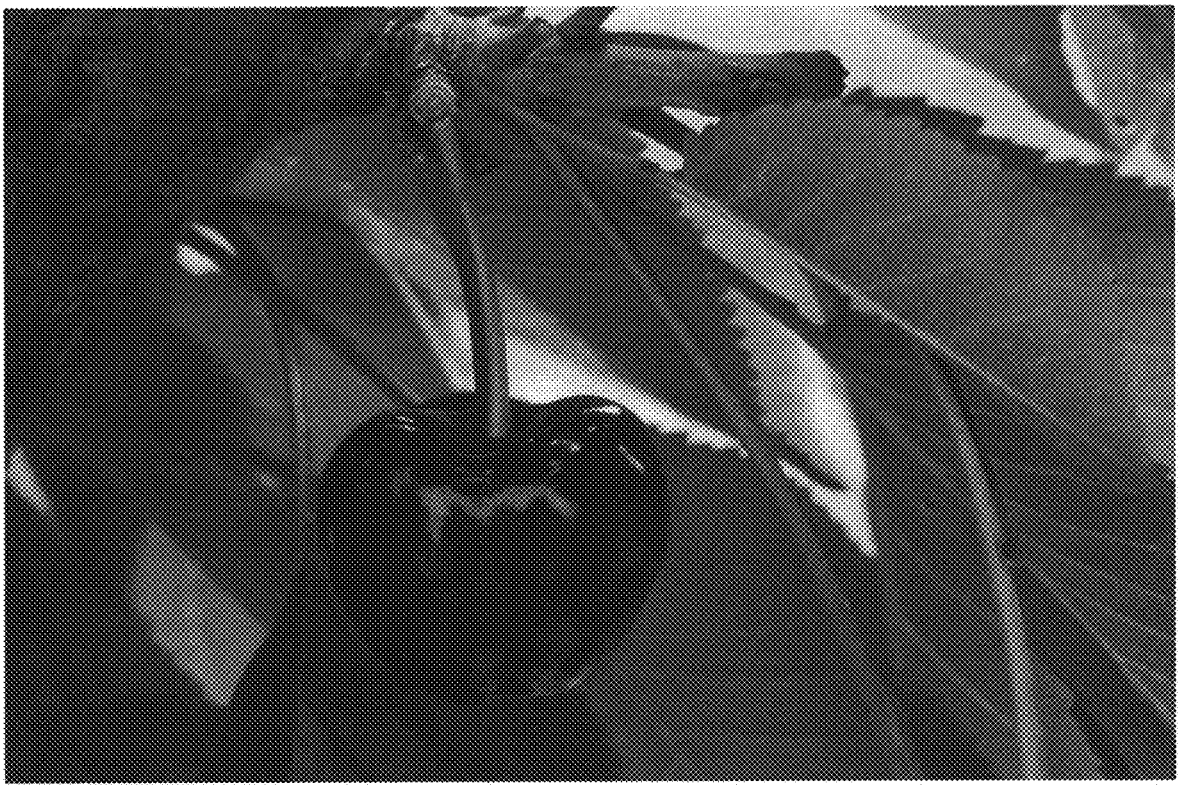
FIG. 1 is a color photograph showing typical specimens of the fruit and stem of 'Prim 22'.
Figure 2:
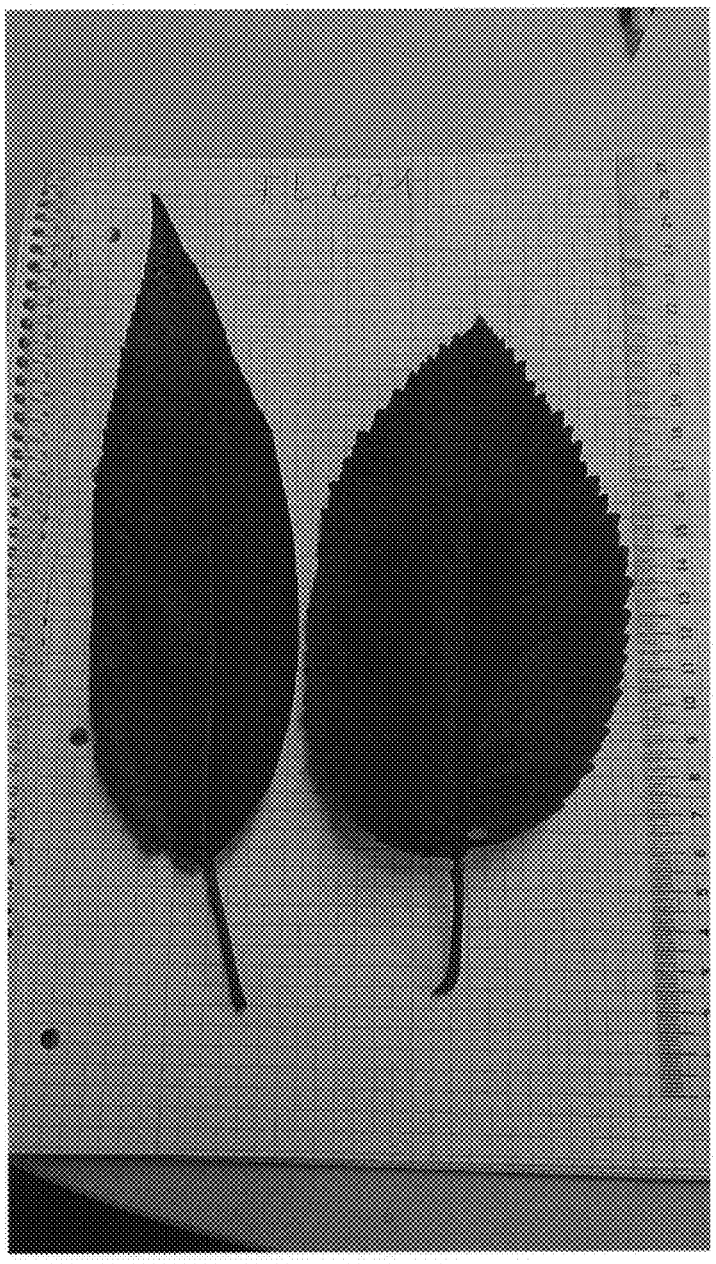
FIG. 2 is a color photograph showing the upper surface of leaves from 'Prim 22'.
Figure 3:
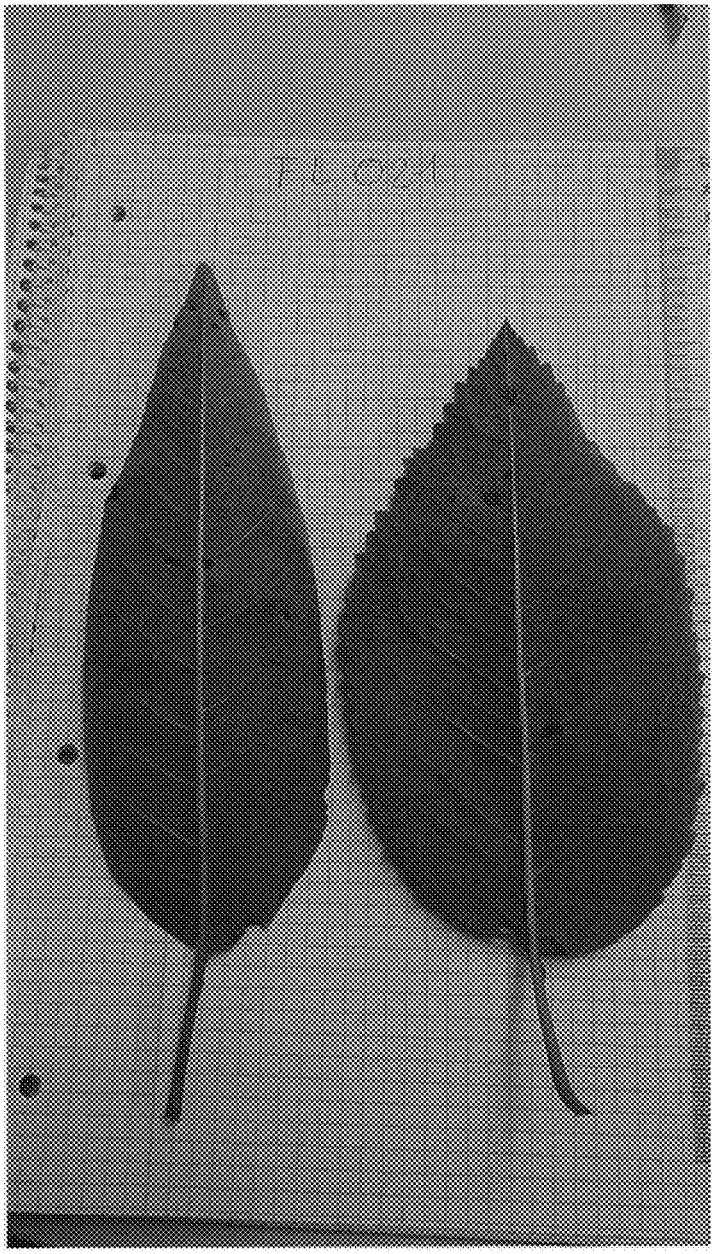
FIG. 3 is a color photograph showing the lower surface of leaves from 'Prim 22'.
Figure 4:
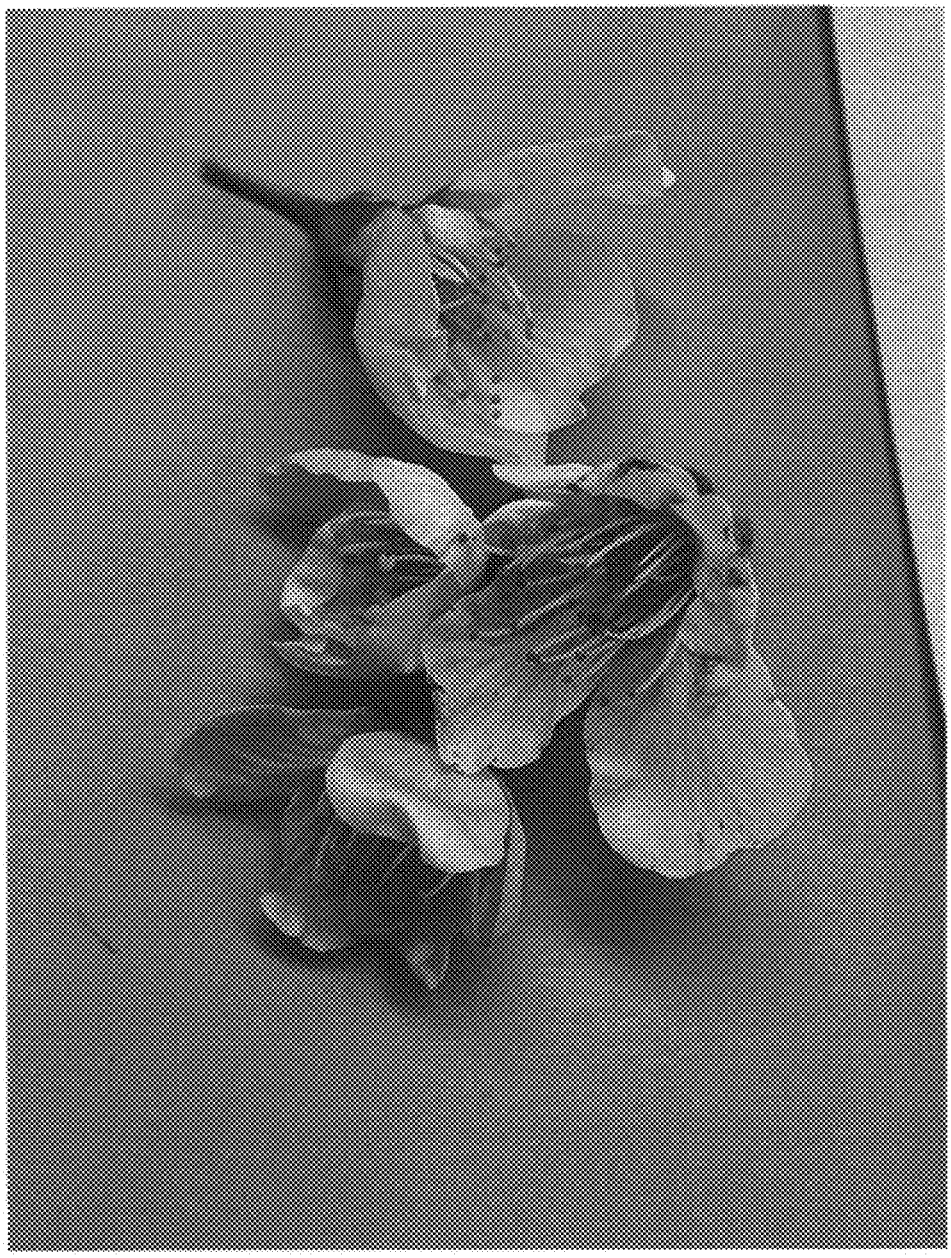
FIG. 4 is a color photograph showing the flower bud and flower of 'Prim 22'.

The following is a detailed description of the botanical characteristics of the new and distinct variety of the sweet cherry tree known by the denomination 'Prim 22'. The detailed description was taken on a seven-year-old tree in Baden-Wuerttemberg, Germany. All colors cited herein refer to The Royal Horticultural Society Mini Colour Chart (The Royal Horticultural Society (RHS), London, 2005 Edition). Where specific dimensions, sizes, colors, and other characteristics are given, it is to be understood that such characteristics are approximations or averages set forth as accurately as practicable.

Tree:

*Vigor.*—Medium.
*Height.*—3 meters.
*Width.*—2 meters.
*Growth habit.*—Drooping, weak.
*Canopy density.*—Medium.
*Form.*—Spreading to drooping.
*Productivity.*—Good.
*Trunk diameter.*—10 cm at 100 cm above ground.
*Trunk surface texture.*—Smooth with prominent lenticels. Lenticel length: about 1-2 cm. Lenticel width: about 0.5 cm. Lenticel color: Grayed Orange 167 A. Lenticel density: medium.
*Bark color.*—Dark brown 200 B.

Branches:

*Diameter.*—1 cm.
*Surface.*—Smooth.
*Form.*—Drooping.
*Bark color.*—Brown 199 A.
*Average angle.*—Prostrate.
*Lenticels.*—Length: approximately 0.1 cm. Width: approximately 0.1 cm. Shape: roundish. Density: medium. Color: Yellow Brown N167 A.

Leaves:

*Arrangement.*—Leaves attach at midpoint of actively growing shoots of the current season's growth.
*Length.*—16.5 cm.
*Width.*—9 cm.
*Form.*—Ovate.
*Texture.*—Leathery, no crisp feeling.
*Thickness.*—Medium.
*Base.*—Rounded.
*Apex.*—Broad, short acuminate.
*Margin.*—Biserrate.
*Pubescence upper surface.*—None.
*Pubescence lower surface.*—None.
*Color young leaves upper surface.*—Green 137 A.
*Color young leaves lower surface.*—Green 146 C.
*Color mature leaves upper surface.*—Dark green 137 A.
*Color mature leaves lower surface.*—Green 146 C.
*Petiole shape.*—Narrow.
*Petiole length.*—3.8 cm.
*Petiole diameter.*—~0.3 cm.
*Petiole color.*—Green 146 C.
*Venation type.*—Pinnate.
*Veins color upper surface.*—Dark green 137 A.
*Veins color lower surface.*—Brown green 152 D.

Flower buds:

*Length.*—0.8 cm.
*Width.*—0.5 cm.
*Color.*—Dark green 144 A.
*Pedicel length.*—0.75 cm.
*Pedicel diameter.*—0.1 cm.
*Pedicel color.*—Dark green 144 A.

Flowers:

*Bloom timing.*—Full flowering Apr. 19 2021 Kressbronn, Germany.
*Blooming period.*—Middle early.
*Pollination requirements.*—Unknown.
*Number of flowers per raceme.*—4-5.
*Fragrance.*—None.
*Petals.*—Number — 5.
*Petals.*—Length — 1.1 cm.
*Petals.*—Width — 1.2 cm.
*Petals.*—Shape — ovoid.
*Petals.*—Margin — repand.
*Petals.*—Texture and appearance — smooth.
*Petals.*—Color — When opening upper surface: White N 999 D. When opening lower surface: White N 999 D. Fully opened upper surface: White N 999 D. Fully opened lower surface: White N 999 D.
*Sepals.*—Shape — oval.
*Sepals.*—Margin — entire.
*Sepals.*—Texture — smooth.
*Sepals.*—Length — 0.7 cm.
*Sepals.*—Width — 0.4 cm.
*Sepals.*—Color upper surface — dark green 144 A.
*Sepals.*—Color lower surface — dark green 144 A.
*Stamens.*—Number per flower — up to 38.
*Filament length.*—0.2-1.5 cm.
*Anthers.*—Kidney shape.
*Anthers.*—Length — 0.3 cm.
*Anthers.*—Color — dark orange yellow 22 A.
*Pollen color.*—Dark orange yellow 21 B.
*Pollen amount.*—Intermediate.
*Pistils.*—Length 1.65 cm.
*Style length.*—1.25 cm.
*Style color.*—Yellow green 145 B.
*Stigma shape.*—Kidney.
*Stigma color.*—Brown green 152 B.
*Pollination requirements.*—S-allele not yet determined, pollinator variety — Prim 3.1.

Fruit:

*Shape.*—Angular to oblate.
*Diameter.*—29.6 mm.
*Skin color.*—Dark purple red 53 A.
*Skin ground color.*—Dark purple red 53 A.
*Skin thickness.*—Medium.
*Skin texture.*—Smooth.
*Skin tendency to crack.*—No.
*Flesh color.*—Dark purple red 184 D.
*Firmness.*—Medium, firm.
*Aroma.*—Typical cherry aroma.
*Eating quality.*—Good.
*Stone length.*—1.1 cm.
*Stone width.*—0.7 cm.
*Stone form.*—Oval.
*Stone color.*—Orange white 159 A.
*Stem length.*—2.5 cm.
*Stem width.*—0.2 cm.
*Stem color.*—Yellow green 145 B.
*Ripening period middle early.*—Jun. 17, 2021.

*Average fruit weight*.—12.1 g.

*Use*.—Fresh market and storage; brix about 17.70 Durofel; good eating quality.

Productivity depends on the density of planting but is about 14 t/ha.

Resistance to pathogens is typical of *Prunus avium* species generally.

What is claimed is:

1. A new and distinct variety of sweet cherry tree named 'Prim 22' having the characteristics substantially as described and illustrated herein.

* * * * *